United States Patent [19]

Foley et al.

[11] Patent Number: 5,470,814
[45] Date of Patent: Nov. 28, 1995

[54] CMS/SIO$_2$/AL$_2$O$_3$ CATALYSTS FOR IMPROVED SELECTIVITY IN THE SYNTHESIS OF AMINES FROM METHANOL AND/OR DIMETHYL ETHER AND AMMONIA

[75] Inventors: Henry C. Foley, Newark; George C. Sonnichsen; Loren D. Brake, both of Wilmintgon; Ravindra K. Mariwala, Newark, all of Del.; David S. Lafyatis, Gent, Belgium

[73] Assignees: University of Delaware, Newark; E. I. Du Pont de Nemours & Co., Inc., Wilmington, both of Del.

[21] Appl. No.: 278,643

[22] Filed: Jul. 21, 1994

Related U.S. Application Data

[62] Division of Ser. No. 100,463, Jul. 30, 1993, Pat. No. 5,354,893.

[51] Int. Cl.$^6$ .............................. B01J 21/18; B01J 21/04
[52] U.S. Cl. ............................................. 502/182; 502/439
[58] Field of Search ........................................ 502/182, 439

[56] References Cited

U.S. PATENT DOCUMENTS

| | | | |
|---|---|---|---|
| 2,017,069 | 10/1935 | Lazier | 260/127 |
| 2,777,881 | 1/1957 | Neuworth | 260/621 |
| 3,384,667 | 5/1968 | Hamilton | 260/585 |
| 3,446,865 | 5/1969 | Roth et al. | 260/669 |
| 4,082,661 | 4/1978 | Aoki et al. | 210/40 |
| 4,206,078 | 6/1980 | Ohorodnik et al. | 262/423 |
| 4,370,503 | 1/1983 | Brake | 564/474 |
| 4,398,041 | 8/1983 | Cochran et al. | 564/479 |
| 4,471,072 | 9/1984 | Leyerle et al. | 502/413 |
| 4,499,201 | 2/1985 | Leyerle | 502/180 |
| 4,528,281 | 7/1985 | Sutt, Jr. | 502/402 |
| 4,713,090 | 12/1987 | Yokoe et al. | 502/402 |
| 4,820,318 | 4/1989 | Dhang et al. | 55/68 |
| 4,916,110 | 4/1990 | Manniso | 502/439 |
| 4,957,897 | 9/1990 | Maroldo et al. | 502/432 |
| 4,970,189 | 11/1990 | Tachibana | 502/183 |
| 5,037,791 | 8/1991 | Comolli et al. | 502/185 |
| 5,294,585 | 3/1994 | Moreau et al. | 502/413 |

FOREIGN PATENT DOCUMENTS

| | | | |
|---|---|---|---|
| 251507 | 11/1987 | Germany. | |
| 251505 | 11/1987 | Germany | 502/182 |
| 8600646 | 10/1987 | Netherlands. | |

OTHER PUBLICATIONS

Henry C. Foley, *Carbon Molecular Sieves Properties and Applications in Perspective*, ACS symposium series, Jun. 5–11, 1988, pp. 335–359.

Lafyatis et al. *Poly (furfuryl alcohol)–Derived Carbon Molecular Sieves: Dependence of Absorptive Properties on Carbonization Temperature, Time, and Poly (ethylene glycol) Additives*. Ind. Eng. Chem. Res., vol. 30, No. 5, 1991, pp. 865–873.

Henry C. Foley, *Carbon Molecular Sieves: Properties and Applications in Perspective*, Perspectives in Molecular Sieve Science, 335–360 (William H. Flankk & Thaddeuss E. Whyte, Jr. ed., 1988).

*Primary Examiner*—Asok Pal
*Assistant Examiner*—Nhat D. Phan
*Attorney, Agent, or Firm*—Connolly & Hutz

[57] ABSTRACT

The present invention relates to an improved catalyst for the selective synthesis of monomethylamine (MMA) and dimethylamine (DMA) at the expense of trimethylamine (TMA) for a starting feed of methanol and/or dimethyl ether and ammonia. The current industrial catalyst for this process is a standard SiO$_2$/Al$_2$O$_3$ material. The present invention combines this standard catalyst with microporous carbon molecular sieves (CMS) to form a composite material (i.e., a CMS/SiO$_2$/Al$_2$O$_3$ material) with higher selectivity for the desired products MMA and DMA. The invention also relates to methods of making the improved catalyst and a process of using the improved catalyst material in the production of MMA and DMA.

15 Claims, 2 Drawing Sheets

CMS/SiO$_2$/Al$_2$O$_3$ CATALYSTS FOR IMPROVED SELECTIVITY IN THE SYNTHESIS OF AMINES FROM METHANOL AND/OR DIMETHYL ETHER AND AMMONIA

CROSS-REFERENCE TO RELATED APPLICATION

The present application is a divisional application of U.S. patent application Ser. No. 08/100,463 filed on Jul. 30, 1993, in the names of Henry C. Foley et al., now U.S. Pat. No. 5,354,893 which issued on Oct. 11, 1994.

BRIEF DESCRIPTION OF THE INVENTION

The present invention relates to an improved catalyst for the selective synthesis of monomethylamine (MMA) and dimethylamine (DMA) at the expense of trimethylamine (TMA) for a starting feed of methanol and/or dimethyl ether and ammonia. The current industrial catalyst for this process is a standard SiO$_2$/Al$_2$O$_3$ material. The present invention combines this standard catalyst with microporous carbon molecular sieves (CMS) to form a composite material (i.e., a CMS/SiO$_2$/Al$_2$O$_3$ material) with higher selectivity for the desired products MMA and DMA. The invention also relates to methods of making the improved catalyst and a process of using the improved catalyst material in the production of MMA and DMA.

BACKGROUND OF THE INVENTION

The production of monomethylamine (MMA), dimethylamine (DMA) and trimethylamine (TMA) is performed industrially by the reaction of methanol and/or dimethyl ether and ammonia (and sometimes recycled methylamines) over amorphous silica-alumina catalysts. The reaction goes toward an equilibrium distribution of products, of which the thermodynamically most favored product is TMA. However, TMA is the least desirable commercial product. Table 1 summarizes the equilibrium product distribution and the market demand for MMA, DMA, and TMA.

TABLE 1

| Equilibrium Product Distribution and Market Demand for Methylamines* | | | |
|---|---|---|---|
| | MMA | DMA | TMA |
| Equilibrium | 17 | 21 | 62 |
| Market | 33 | 53 | 14 |

*400° C., 1:1 NH$_3$:CH$_3$OH feed ratio

The discrepancy between the market demand and the normal product distribution of methylamines has created interest in developing catalysts with higher selectivity for the desired products MMA and DMA at the expense of TMA.

SUMMARY OF THE INVENTION

The present invention relates to an improved catalyst for the selective synthesis of monomethylamine (MMA) and dimethylamine (DMA) at the expense of trimethylamine (TMA) for a starting feed of methanol and/or dimethyl ether and ammonia. The current industrial catalyst for this process is a standard SiO$_2$/Al$_2$O$_3$ material. The present invention combines this standard type of catalyst with microporous carbon molecular sieves (CMS) to form a composite material with higher selectivity for the desired products MMA and DMA. The invention also relates to methods of making the improved catalyst and a process of using the improved catalyst material in the production of MMA and DMA.

The active catalytic phase of the CMS/SiO$_2$/Al$_2$O$_3$ material of the present invention is the solid acid SiO$_2$/Al$_2$O$_3$, which is the commercial catalyst used in the synthesis of amines from methanol and/or dimethyl ether and ammonia. The carbon molecular sieves (CMS) of the present invention are synthesized from a precursor material. Examples of preferred precursor materials are polyacrylonitrile (PAN), phenol formaldehyde resin (PFR), polyvinylidene chloride (PVDC), polyfurfuryl alcohol (PFA) or any combination of the above. A preferred method of forming the carbon molecular sieves used in the production of the CMS/SiO$_2$/Al$_2$O$_3$ material of the present invention is the pyrolysis of polyfurfuryl alcohol. However, any known method of forming microporous carbon materials or carbon molecular sieves can be used in the production of the CMS/SiO$_2$/Al$_2$O$_3$ material of the present invention.

The present invention also includes methods of making the CMS/SiO$_2$/Al$_2$O$_3$ materials. Specifically, as described below, there are three preferred methods of making the material.

The first method includes mixing the SiO$_2$/Al$_2$O$_3$ catalyst material, in powder form, with a precursor material to form an initial mixture. The initial mixture is then heated for a period of time which is sufficient to convert (i.e., by pyrolysis) a portion of the precursor material to CMS. Most, if not all, of the remainder of the precursor material is vaporized during this first pyrolysis step. The material formed in the first pyrolysis step is a CMS/SiO$_2$/Al$_2$O$_3$ material. After the first pyrolysis step, the CMS/SiO$_2$/Al$_2$O$_3$ material is typically washed with, for example, acetone in order to remove any residual precursor material and/or materials that are not attached to the SiO$_2$/Al$_2$O$_3$ catalyst material. The washed CMS/SiO$_2$/Al$_2$O$_3$ material can be used as a catalyst in methylamines synthesis. However, in a highly preferred embodiment of the present invention, the CMS/SiO$_2$/Al$_2$O$_3$ material formed in the first pyrolysis step (after washing with acetone) is mixed with additional precursor material to form a second mixture. The second mixture is then heated for a period of time which is sufficient to form additional CMS material (by pyrolysis) and vaporize most, if not all, of the remainder of the precursor material. The material obtained at the end of the second pyrolysis step contains more CMS material than the material formed at the end of the first pyrolysis step.

In another preferred embodiment of the present invention, the CMS/SiO$_2$/Al$_2$O$_3$ material formed in the first pyrolysis step is ground to powder (after washing with acetone) before being mixed with the additional precursor material to form the second mixture.

In either of the two above-described embodiments of the first method, after the second mixture has been heated (i.e., subjected to pyrolysis) to form CMS/SiO$_2$/Al$_2$O$_3$ material, it may be necessary to comminute the CMS/SiO$_2$/Al$_2$O$_3$ material to form a particulate CMS/SiO$_2$/Al$_2$O$_3$ material that is suitable for use as a catalyst material. However, in another embodiment of the present invention, the material obtained after the second mixture is heated is not comminuted before being used as a catalyst material. In either case, the CMS material is located primarily on the external surface of each particle of the SiO$_2$/Al$_2$O$_3$ material as a distinct layer which isolates the SiO$_2$/Al$_2$O$_3$ catalyst material from the surrounding atmosphere. A representative particle is shown in FIG. 1 where the SiO$_2$/Al$_2$O$_3$ catalyst is indicated as (1) and the CMS layer as (2). Before being used as a catalyst material, the CMS/SiO$_2$/Al$_2$O$_3$ material is typically washed with, for example, acetone. It should be noted that additional pyrolysis steps can be performed, if desired, to obtain additional CMS material on the surface of the previously formed CMS/SiO$_2$/Al$_2$O$_3$ particles. Such additional pyrolysis steps would include mixing the CMS/SiO$_2$/Al$_2$O$_3$ material formed in the previous pyrolysis step with additional precursor material and then heating the mixture to convert at least a portion of the precursor material into additional CMS material. After each pyrolysis step, the CMS/SiO$_2$/Al$_2$O$_3$ material is typically washed with, for example, acetone.

The second method includes dropping hot pellets of the SiO$_2$/Al$_2$O$_3$ catalyst material into a body of precursor material located within a suitable container at ambient temperature. After the hot pellets have been quenched within the precursor material, the contents of the container are poured over a screen which retains the pellets. The recovered pellets are then rinsed thoroughly with, for example, acetone. The surface of the pellets contain CMS material formed when the hot pellets converted some of the surrounding precursor material to CMS. The process can be repeated several times to increase the amount of CMS in the surface of the pellets. As shown in FIG. 2, the final product of this process is a pellet of SiO$_2$/Al$_2$O$_3$ catalyst material (1) that has an external surface that is covered with a layer of CMS material (2). The CMS layer may also extend to a point that is within the body of the SiO$_2$/Al$_2$O$_3$ pellet. In either case, the CMS layer isolates the SiO$_2$/Al$_2$O$_3$ catalyst material from the surrounding atmosphere.

The third method includes mixing pellets of the SiO$_2$/Al$_2$O$_3$ catalyst material with precursor material and heating the mixture to convert (i.e., by pyrolysis) at least a portion of the precursor material to CMS material. The material formed in this first pyrolysis step is a CMS/SiO$_2$/Al$_2$O$_3$ material. After the first pyrolysis step, the CMS/SiO$_2$/Al$_2$O$_3$ material is typically washed with, for example, acetone. The washed CMS/SiO$_2$/Al$_2$O$_3$ material can be used as a catalyst in methylamines synthesis. However, in a highly preferred embodiment of the present invention, the CMS/SiO$_2$/Al$_2$O$_3$ material formed in the first pyrolysis step is subjected to one or more additional pyrolysis steps wherein each pyrolysis step includes mixing the CMS/SiO$_2$/Al$_2$O$_3$ material formed in the previous pyrolysis step with additional precursor material and then heating the mixture to convert at least a portion of the precursor material into additional CMS material. After each pyrolysis step, the CMS/SiO$_2$/Al$_2$O$_3$ material is typically washed with, for example, acetone. As shown in FIG. 2, the final product of this process is a pellet of SiO$_2$/Al$_2$O$_3$ catalyst material (1) that has an external surface that is covered with a layer of CMS material (2). The CMS layer may also extend to a point that is within the body of the SiO$_2$/Al$_2$O$_3$ pellet. In either case, the CMS layer isolates the SiO$_2$/Al$_2$O$_3$ catalyst material from the surrounding atmosphere.

The present invention also includes a method of using the CMS/SiO$_2$/Al$_2$O$_3$ material in a process which comprises the following steps:

a) feeding ammonia and methanol and/or dimethyl ether to a reactor containing a CMS/SiO$_2$/Al$_2$O$_3$ material;

b) reacting the ammonia and methanol and/or dimethyl ether within the reactor to form monomethylamine (MMA), dimethylamine (DMA) and trimethylamine (TMA), wherein the molar ratio (MMA+DMA)/TMA, defined as the combined amount of MMA and DMA removed from the reactor (in moles) divided by the amount of TMA removed from the reactor (in moles), has a value which is larger than would be obtained in an equivalent reactor under equivalent conditions using the standard SiO$_2$/Al$_2$O$_3$ catalyst material; and c) collecting the MMA, DMA and TMA produced in the reactor.

In a preferred embodiment of the present invention, the MMA, DMA and TMA are separated from one another by distillation of the crude product stream exiting the reactor.

DETAILED DESCRIPTION OF THE INVENTION

Figure 1:
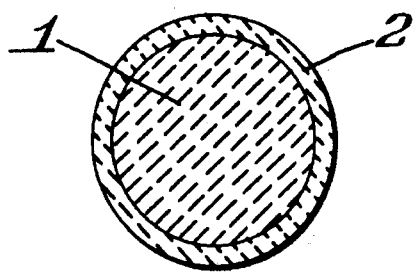
FIG. 1 is a cross-sectional view of a CMS/SiO$_2$/Al$_2$O$_3$ particle.

The present invention relates to an improved catalyst for the selective synthesis of monomethylamine (MMA) and dimethylamine (DMA) at the expense of trimethylamine (TMA) for a starting feed of methanol and/or dimethyl ether and ammonia. The current industrial catalyst for this process is a standard SiO$_2$/Al$_2$O$_3$ material. The present invention combines this standard type of catalyst with microporous carbon molecular sieves (CMS) to form a composite material with higher selectivity for the desired products MMA and DMA. The invention also relates to methods of making the improved catalyst and a process of using the improved catalyst material in the production of MMA and DMA.

The active catalytic phase of the CMS/SiO$_2$/Al$_2$O$_3$ material of the present invention is the solid acid SiO$_2$/Al$_2$O$_3$, which is the commercial catalyst used in the synthesis of amines from methanol and/or dimethyl ether and ammonia. The carbon molecular sieves (CMS) of the present invention are synthesized from a precursor material. Examples of preferred precursor materials are polyacrylonitrile (PAN), phenol formaldehyde resin (PFR), polyvinylidene chloride (PVDC), polyfurfuryl alcohol (PFA) or any combination of the above. A preferred method of forming the carbon molecular sieves used in the production of the CMS/SiO$_2$/Al$_2$O$_3$ material of the present invention is the pyrolysis of polyfurfuryl alcohol (e. g., Durez resin #16470 obtained from Occidental Chemicals). For certain embodiments of the present invention, it is desirable to use polyfurfuryl alcohol having a high molecular weight (e.g., PFA with a molecular weight that is higher than commercial resins such as Durez resin #16470 obtained from Occidental Chemicals). However, any known method of forming microporous carbon materials or carbon molecular sieves can be used in the production of the CMS/SiO$_2$/Al$_2$O$_3$ material of the present invention.

The present invention also includes methods of making the CMS/SiO$_2$/Al$_2$O$_3$ materials. Specifically, as described below, there are three preferred methods of making the material.

The first method includes mixing the SiO$_2$/Al$_2$O$_3$ catalyst material, in powder form (e.g., about −400 mesh), with a precursor material to form an initial mixture. A preferred composition of the initial mixture is about three parts by weight $SiO_2/Al_2O_3$ and four parts by weight of the precursor material. The initial mixture is then heated for a period of time which is sufficient to convert (i.e., by pyrolysis) a portion (e.g., about 25% by weight) of the precursor material to CMS. Most, if not all, of the remainder of the precursor material is vaporized during this first pyrolysis step. A preferred method of performing the first pyrolysis step includes heating the initial mixture at about 0.1° C. to 2° C. per minute to a holding temperature of from about 400° C. to about 800° C., preferably from about 450° C. to about 600° C., and more preferably about 500° C., and soaking the mixture at the holding temperature for at least one hour in inert gas (e.g., helium, argon or, possibly, nitrogen), preferably flowing inert gas. The preferred soaking time is from about 1 to 8 hours and the preferred inert gas is helium. The material formed in the first pyrolysis step is a $CMS/SiO_2/Al_2O_3$ material. After the first pyrolysis step, the $CMS/SiO_2/Al_2O_3$ material is typically washed with, for example, acetone in order to remove any residual precursor material and/or materials that are not attached to the $SiO_2/Al_2O_3$ catalyst material. The washed $CMS/SiO_2/Al_2O_3$ material can be used as a catalyst in methylamines synthesis. However, in a highly preferred embodiment of the present invention, the $CMS/SiO_2/Al_2O_3$ material formed in the first pyrolysis step (after washing with acetone) is mixed with additional precursor material to form a second mixture. A preferred composition of the second mixture is about three parts by weight of the $CMS/SiO_2/Al_2O_3$ material from the first pyrolysis step and four parts by weight of additional precursor material. The second mixture is then heated for a period of time which is sufficient to form additional CMS material (by pyrolysis) and vaporize most, if not all, of the remainder of the precursor material. A preferred method of performing the second pyrolysis step is to subject the second mixture to the same conditions used in the first pyrolysis step. The material obtained at the end of the second pyrolysis step contains more CMS material than the material formed at the end of the first pyrolysis step.

In another preferred embodiment of the present invention, the $CMS/SiO_2/Al_2O_3$ material formed in the first pyrolysis step is ground to powder (e.g., about −170 mesh; after washing with acetone) before being mixed with the additional precursor material to form the second mixture.

In either of the two above-described embodiments of the first method, after the second mixture has been heated (i.e., subjected to pyrolysis) to form $CMS/SiO_2/Al_2O_3$ material, it may be necessary to comminute the $CMS/SiO_2/Al_2O_3$ material to form a particulate $CMS/SiO_2/Al_2O_3$ material that is suitable for use as a catalyst material. For example, the $CMS/SiO_2/Al_2O_3$ material can be sized to any appropriate size before being used as a catalyst material. Although applicants do not wish to be limited to any particular particle size for the catalyst material, particles that have been sized to less than 20 and greater than 50 mesh (<20, >50 mesh) have been found to be useful. However, it is not necessary that the $CMS/SiO_2/Al_2O_3$ material be comminuted before being used as a catalyst. For example, in another embodiment of the present invention, the material obtained after the second mixture is heated is not comminuted before being used as a catalyst material. In either case (i.e., comminuted or non-comminuted catalyst material), the CMS material is located primarily on the external surface of each particle of the $SiO_2/Al_2O_3$ material as a distinct layer which isolates the $SiO_2/Al_2O_3$ catalyst material from the surrounding atmosphere. A representative particle is shown in FIG. 1 where the $SiO_2/Al_2O_3$ catalyst is indicated as (1) and the CMS layer as (2). Before being used as a catalyst material, the $CMS/SiO_2/Al_2O_3$ material is typically washed with, for example, acetone. It should be noted that additional pyrolysis steps can be performed, if desired, to obtain additional CMS material on the surface of the previously formed $CMS/SiO_2/Al_2O_3$ particles. Such additional pyrolysis steps would include mixing the $CMS/SiO_2/Al_2O_3$ material formed in the previous pyrolysis step with additional precursor material and then heating the mixture to convert at least a portion of the precursor material into additional CMS material. After each pyrolysis step, the $CMS/SiO_2/Al_2O_3$ material is typically washed with, for example, acetone.

Figure 2:
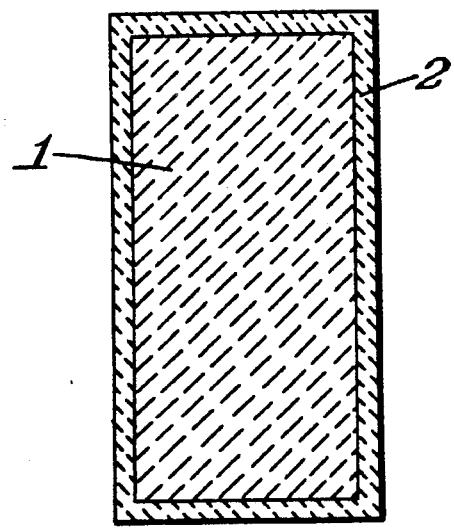
FIG. 2 is a cross-sectional view of a CMS/SiO$_2$/Al$_2$O$_3$ pellet.

The second method includes dropping hot pellets of the $SiO_2/Al_2O_3$ catalyst material into a body of precursor material located within a suitable container at ambient temperature. The pellets of the $SiO_2/Al_2O_3$ catalyst material may be preheated by any suitable means before they are dropped into the precursor material. One preferred method of preheating the pellets includes placing the pellets in a stainless steel cylinder located above the container which holds the body of precursor material and heating the cylinder to about 600° C. for about two hours while flowing nitrogen through the cylinder. In a preferred embodiment of the present invention, the preheated pellets are dropped into the precursor material in batches of about 20–40. Larger or smaller batches can be used depending on the size of the container and the amount of precursor material located within the container. After the hot pellets have been quenched within the precursor material, the contents of the container are poured over a screen which retains the pellets. The recovered pellets are then rinsed thoroughly with, for example, acetone. The surface of the pellets contain CMS material formed when the hot pellets converted some of the surrounding precursor material to CMS. The process can be repeated several times to increase the amount of CMS in the surface of the pellets. As shown in FIG. 2, the final product of this process is a pellet of $SiO_2/Al_2O_3$ catalyst material (1) that has an external surface that is covered with a layer of CMS material (2). The CMS layer may also extend to a point that is within the body of the $SiO_2/Al_2O_3$ pellet. In either case, the CMS layer isolates the $SiO_2/Al_2O_3$ catalyst material from the surrounding atmosphere.

The third method includes mixing pellets of the $SiO_2/Al_2O_3$ catalyst material with precursor material and heating the mixture to convert (i.e., by pyrolysis) at least a portion of the precursor material to CMS material. The material formed in this first pyrolysis step is a $CMS/SiO_2/Al_2O_3$ material. After the first pyrolysis step, the $CMS/SiO_2/Al_2O_3$ material is typically washed with, for example, acetone. The washed $CMS/SiO_2/Al_2O_3$ material can be used as a catalyst in methylamines synthesis. However, in a highly preferred embodiment of the present invention, the $CMS/SiO_2/Al_2O_3$ material formed in the first pyrolysis step is subjected to one or more additional pyrolysis steps wherein each pyrolysis step includes mixing the $CMS/SiO_2/Al_2O_3$ material formed in the previous pyrolysis step with additional precursor material and then heating the mixture to convert at least a portion of the precursor material into additional CMS material. After each pyrolysis step, the $CMS/SiO_2/Al_2O_3$ material is typically washed with, for example, acetone. As shown in FIG. 2, the final product of this process is a pellet of $SiO_2/Al_2O_3$ catalyst material (1) that has an external surface that is covered with a layer of CMS material (2). The CMS layer may also extend to a point that is within the body of the $SiO_2/Al_2O_3$ pellet. In either case, the CMS layer isolates the $SiO_2/Al_2O_3$ catalyst material from the surrounding atmosphere.

In a preferred embodiment$^{MMA}$ of the present invention, all or substantially all of the external surfaces of the particles or pellets of the $SiO_2/Al_2O_3$ catalyst material are completely covered with the CMS material as shown in FIG. 1 and FIG. 2. However, the present invention is also directed to embodiments wherein the CMS material only partially covers the external surfaces of the $SiO_2/Al_2O_3$ catalyst material or only completely covers the external surfaces of a portion of the catalyst particles or pellets. In these latter embodiments of the present invention, the selectivity of the CMS/$SiO_2$/$Al_2O_3$ catalyst material will be reduced in comparison to catalyst materials wherein the entire external surfaces of the $SiO_2/Al_2O_3$ catalyst particles or pellets are covered with CMS material (i.e., the molar ratio of (MMA+DMA)/TMA, which is a measure of the selectivity of the catalyst materials, will be reduced in the CMS/$SiO_2/Al_2O_3$ catalyst materials wherein the external surfaces of the $SiO_2/Al_2O_3$ catalyst particles or pellets are not completely covered with CMS material). However, the selectivity of the CMS/$SiO_2$/$Al_2O_3$ catalyst materials in these less preferred embodiments of the present invention will still be higher than the standard $SiO_2/Al_2O_3$ catalyst material.

Preferably, the $SiO_2/Al_2O_3$ catalyst material should be highly porous so that a large surface area of the catalyst is available for the methylamine synthesis reaction. Moreover, it is preferable that the CMS coating be located on the external surface of the catalyst particles or pellets and not extend significantly into the pore structure of each catalyst particle or pellet. Although some infiltration of the CMS material into the pore structure of the catalyst particles or pellets is inevitable, this infiltration may reduce the activity of the catalyst material by limiting the surface area of the $SiO_2/Al_2O_3$ catalyst that is readily available to the methanol and/or dimethyl ether and ammonia starting materials.

Although it is possible to use the catalyst in many different reactor setups, a particularly preferred setup is a fixed-bed reactor (i.e., a fixed bed of the catalyst within the reactor).

In a highly preferred embodiment of the present invention, the CMS/$SiO_2/Al_2O_3$ catalyst comprises a layer of CMS material which forms at least a partial coating on the surface of a $SiO_2/Al_2O_3$ catalyst material that is in the form of cylindrical pellets, extrudate or any other form with a vast geometric surface area. The size of the resulting CMS/$SiO_2$/$Al_2O_3$ catalyst particle is selected according to recognized chemical engineering principles. A particularly desirable size for the CMS/$SiO_2/Al_2O_3$ particles is in the range of from about 3–130 mm (⅛ inch to about ½ inch) in all dimensions. The pore volume of the $SiO_2/Al_2O_3$ catalyst core and its total surface area are likewise a matter of choice and can be selected to accommodate the particular system being utilized. A particularly desirable pore volume for the $SiO_2/Al_2O_3$ catalyst core is from about 0.2 to 0.8 cc/g and a particularly desirable total surface area for the $SiO_2/Al_2O_3$ catalyst core is from about 100 to 250 m$^2$/g.

The present invention also includes a method of using the CMS/$SiO_2/Al_2O_3$ material in a process which comprises the following steps:

a) feeding ammonia and methanol and/or dimethyl ether to a reactor containing a CMS/$SiO_2/Al_2O_3$ material;

b) reacting the ammonia and methanol and/or dimethyl ether within the reactor to form monomethylamine (MMA), dimethylamine (DMA) and trimethylamine (TMA), wherein the molar ratio (MMA+DMA)/TMA, defined as the combined amount of MMA and DMA removed from the reactor (in moles) divided by the amount of TMA removed from the reactor (in moles), has a value which is larger than would be obtained in an equivalent reactor under equivalent conditions using the standard $SiO_2/Al_2O_3$ catalyst material (i.e., a $SiO_2/Al_2O_3$ catalyst material which is identical to the CMS/$SiO_2/Al_2O_3$ catalyst material except that it does not contain any CMS material); and c) collecting the MMA, DMA and TMA produced in the reactor.

In a preferred embodiment of the present invention, the MMA, DMA and TMA are separated from one another by distillation of the crude product stream exiting the reactor.

As shown in Examples 7 and 8, the CMS/$SiO_2/Al_2O_3$ material of the present invention provides superior selectivity in comparison to the standard $SiO_2/Al_2O_3$ catalyst material in regard to the production of MMA and DMA at the expense of TMA using a starting feed of methanol and/or dimethyl ether and ammonia. In general, the selectivity (i.e., the molar ratio of (MMA+DMA)/TMA) of the standard $SiO_2/Al_2O_3$ catalyst material that is presently used in methylamine synthesis (i.e., AL-1602 obtained from Harshaw Chemical Co. or Engelhard Corp.; 94% by weight alumina and 6% by weight silica) at about 400° C. is about 1.05 at equilibrium conversion (i.e., about 95.8% methanol conversion). The selectivity of the standard $SiO_2/Al_2O_3$ catalyst material at 400° C. approaches 2.0 at low methanol conversion (e.g., 60–65%). In contrast, the selectivity of the CMS/$SiO_2/Al_2O_3$ catalyst materials of the present invention in methylamine synthesis at about 400° C. is greater than 2.0 and preferably in the range of from about 2.30 to 3.30 at about 95% methanol conversion. Moreover, the selectivity of the CMS/$SiO_2/Al_2O_3$ catalyst materials of the present invention in methylamine synthesis at about 400° C. can exceed 5.0 at methanol conversions of about 64%. Therefore, since the CMS/$SiO_2/Al_2O_3$ catalyst materials of the present invention demonstrate a dramatic improvement in selectivity for the desired products MMA and DMA in methylamine synthesis (i.e., in comparison to the standard $SiO_2/Al_2O_3$ catalyst), these new catalyst materials should be very useful in the commercial production of methylamines.

Although applicants do not wish to be bound by any theory concerning the reason for the superior selectivity of the CMS/$SiO_2/Al_2O_3$ material, it is believed that the pore structure of the CMS material is permeable to the methanol (and/or dimethyl ether), ammonia, MMA and DMA but is not easily permeable to the TMA (i.e., the CMS material has shape selective properties). Accordingly, the methanol and/or dimethyl ether and ammonia, in vapor form, pass through the CMS layer from the surrounding atmosphere and contact the $SiO_2/Al_2O_3$ catalyst material which results in the production of MMA, DMA, and TMA. The MMA and DMA having respective diameters of about 4 Å and 4.5 Å, then escape from the $SiO_2/Al_2O_3$ catalyst material by diffusing through the pore structure of the CMS layer to the surrounding atmosphere where they are removed from the system in the product stream. The TMA molecules, which have a diameter of about 5 Å, cannot easily pass through the pore structure of the CMS layer, which has a median pore size of about 5 Å, and therefore a portion of the TMA molecules remain trapped within the porosity of the catalyst particles at any given time during the methylamine production process. This build-up of TMA within the porosity of the catalyst particles results in a decrease in the amount of TMA that appears in the product stream and, correspondingly, results in an increase in the ratio of MMA and DMA to TMA (i.e., (MMA+DMA)/TMA) in the product stream.

In a preferred embodiment of the present invention, all or substantially all of the external surfaces of the particles or pellets of the $SiO_2/Al_2O_3$ catalyst material are completely covered with the CMS material as shown in FIG. 1 and FIG. 2. However, the present invention is also directed to embodiments wherein the CMS material only partially covers the external surfaces of the $SiO_2/Al_2O_3$ catalyst material or only completely covers the external surfaces of a portion of the catalyst particles or pellets. In these latter embodiments of the present invention, the selectivity of the $CMS/SiO_2/Al_2O_3$ catalyst material will be reduced in comparison to catalyst materials wherein the entire external surfaces of the $SiO_2/Al_2O_3$ catalyst particles or pellets are covered with CMS material (i.e., the molar ratio of (MMA+DMA)/TMA, which is a measure of the selectivity of the catalyst materials, will be reduced in the $CMS/SiO_2/Al_2O_3$ catalyst materials wherein the external surfaces of the $SiO_2/Al_2O_3$ catalyst particles or pellets are not completely covered with CMS material). However, the selectivity of the $CMS/SiO_2/Al_2O_3$ catalyst materials in these less preferred embodiments of the present invention will still be higher than the standard $SiO_2/Al_2O_3$ catalyst material.

Preferably, the $SiO_2/Al_2O_3$ catalyst material should be highly porous so that a large surface area of the catalyst is available for the methylamine synthesis reaction. Moreover, it is preferable that the CMS coating be located on the external surface of the catalyst particles or pellets and not extend significantly into the pore structure of each catalyst particle or pellet. Although some infiltration of the CMS material into the pore structure of the catalyst particles or pellets is inevitable, this infiltration may reduce the activity of the catalyst material by limiting the surface area of the $SiO_2/Al_2O_3$ catalyst that is readily available to the methanol and/or dimethyl ether and ammonia starting materials.

The belief that the transport of the TMA through the pore structure of the CMS material is hindered relative to the MMA and DMA is supported by the observation that when MMA, DMA and TMA are passed through a packed column of pure CMS material, MMA and DMA are retained by the CMS material but TMA is not retained. This inability of the TMA to diffuse into the pore structure of the CMS material may also explain why the TMA has difficulty escaping the CMS coated $SiO_2/Al_2O_3$ catalyst particles or pellets when the TMA is formed inside of the catalyst and has to pass through the CMS material to enter the product stream. Therefore, when the $CMS/SiO_2/Al_2O_3$ material of the present invention is used in the amine synthesis reaction, the more rapidly diffusing MMA and DMA are produced at a global rate greater than the more slowly diffusing TMA.

Although the present invention is primarily directed to the use of the $CMS/SiO_2/Al_2O_3$ catalysts in methylamine synthesis, it is also possible to use the shape selective $CMS/SiO_2/Al_2O_3$ catalysts in other reaction systems to improve the selectivity of the system for the desired products. For example, the $CMS/SiO_2/Al_2O_3$ catalysts of the present invention could be used for the selective synthesis of para-xylene at the expense of meta-xylene and ortho-xylene for a starting feed of methanol and toluene. The use of the $CMS/SiO_2/Al_2O_3$ catalysts in this reaction system would lead to a molar ratio defined as (moles para-xylene)/(moles ortho-xylene+moles metaxylene) that would have a value which is larger than would be obtained in an equivalent reactor under equivalent conditions using a standard $SiO_2/Al_2O_3$ catalyst material (i.e., a $SiO_2/Al_2O_3$ catalyst material that is identical to the $CMS/SiO_2/Al_2O_3$ catalyst material but without the CMS coating).

The following examples are intended to illustrate several preferred embodiments of the present invention. The examples should not be interpreted as limiting the scope of the present invention to the specific embodiments described therein.

EXAMPLE 1

This Example shows the formation of pure CMS material. The CMS material formed in this Example was used to determine whether the CMS material itself was active (i.e., would react with any of the feed materials) in the methylamines system. As shown in this Example, the CMS material was found to be inactive with respect to the feed materials involved in methylamines synthesis.

Figure 3:
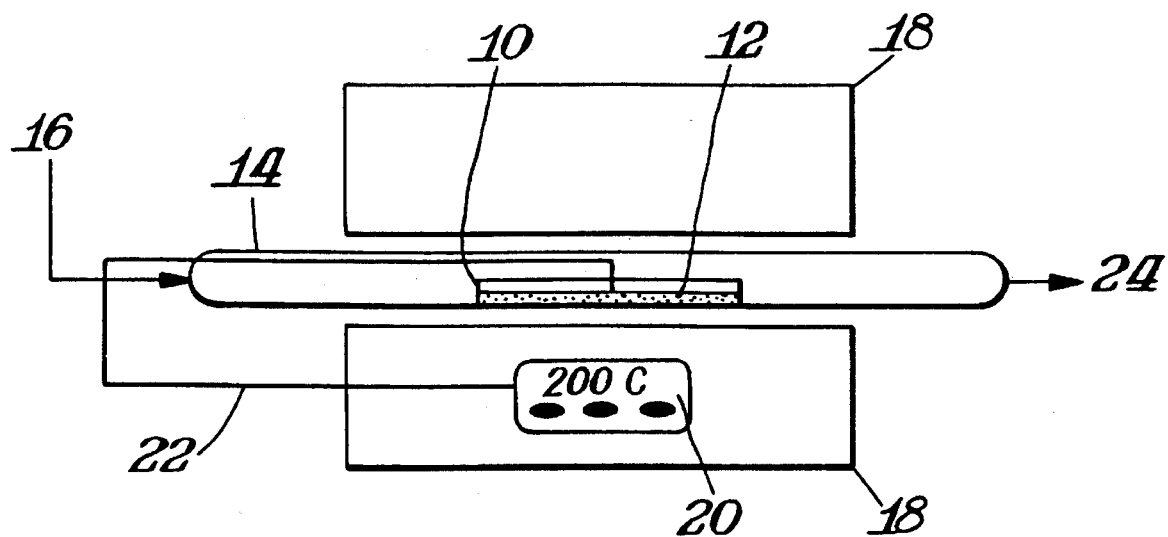
FIG. 3 is a schematic of the quartz reactor used in Examples 1–6 of the present patent application.
Figure 4:
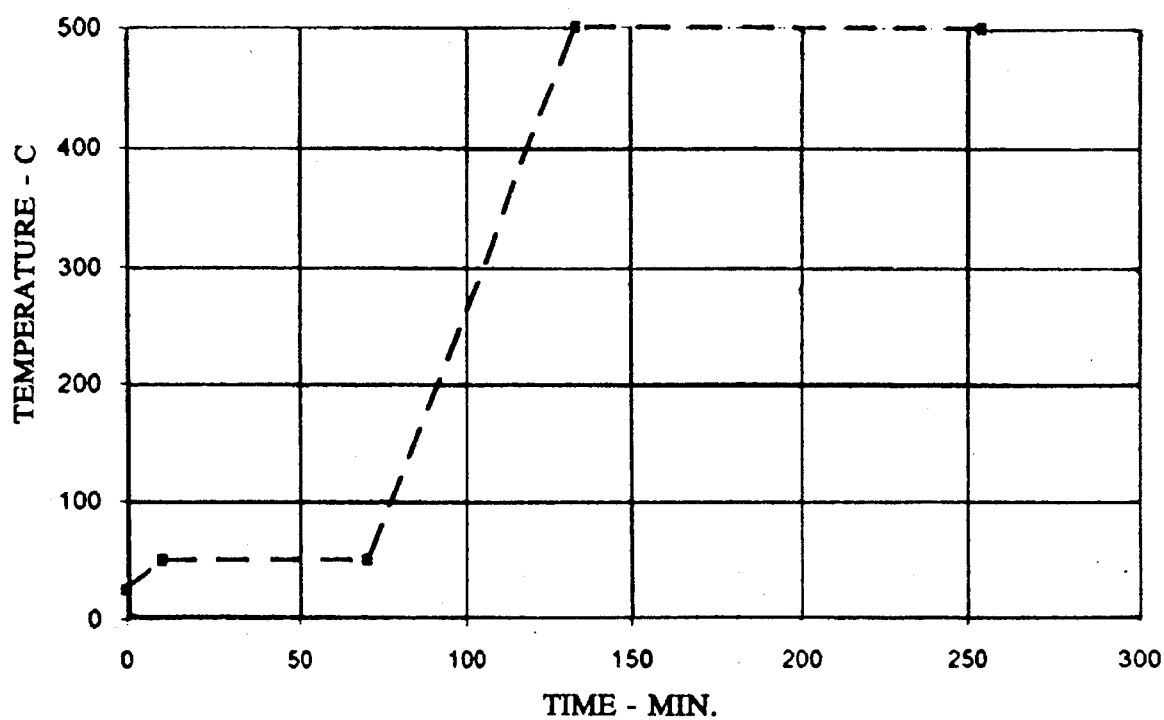
FIG. 4 is a graphical representation of the temperature profile used in Examples 1–6 of the present patent application.

80.5 grams of polyfurfurylalcohol (PFA) resin (obtained from Occidental Chemicals—Durez resin #16470—and having a viscosity of 200 cp and a specific gravity of 1.21 at room temperature) was placed in a quartz boat. The quartz boat was then placed in a quartz reactor. FIG. 3 shows the schematic of the reactor. Specifically, in FIG. 3, the quartz boat is shown as 10, the PFA resin is shown as 12 and the quartz reactor is shown as 14. High purity helium was flowed through the reactor at 0.25 liters/min during the heating cycle and the reactor was purged with helium for 5 minutes prior to the start of the heating cycle. The helium input is shown by arrow 16 in FIG. 3. After the helium purge, the reactor was heated by a single zone Lindbergh furnace 18 controlled by an Omega temperature profile controller 20 including a thermocouple 22. The helium and gaseous pyrolysis products exit the reactor tube at 24. The temperature profile used is depicted in FIG. 4. The ramp rate used was 7° C./min. and the final temperature reached was 500° C. At 500° C. the material in the quartz boat was soaked for 2 hours. The material was then allowed to cool under helium to room temperature (about 20° C.). After reaching room temperature, the material was washed with acetone and dried overnight in an air oven at 100° C. About 20.1 grams of material was obtained after the drying step.

Analysis of the material indicated that it was carbon molecular sieve material resulting from the pyrolysis of the original PFA resin.

The above-described CMS material was tested for methylamines synthesis activity at three temperatures: 325° C., 360° C. and 400° C. at 200 psig pressure with a 1:1 molar ratio of methanol and ammonia. The only components found in the product stream were methanol and ammonia. There was no indication of methylamines being formed. This indicates that the CMS material used in the present invention is inert under methylamines synthesis conditions.

EXAMPLE 2

Silica/alumina catalyst AL-1602 (94% by weight alumina and 6% by weight silica) obtained from Hershaw Chemical Company or Engelhard Corp. was calcined in air for 24 hours at 600° C. and then crushed in a ball mill overnight to obtain −400 mesh powder. 6.1 grams of the −400 mesh silica/alumina powder was mixed with 36.7 grams of polyfurfuryl alcohol (PFA) resin obtained from Occidental Chemicals (Durez resin #16470). The PFA resin had a viscosity of 200 cp and a specific gravity of 1.21 at room temperature. The mixture was then placed in a quartz boat, about 7 inches long and 0.75 inches deep. The quartz boat was placed in a 2.5 inch diameter by 40 inch long quartz reactor. FIG. 3 shows the schematic of the reactor. Helium was flowed through the reactor at 0.25 liters/rain during the heating cycle and the reactor was purged with helium for 5 minutes prior to the start of the heating cycle. After the helium purge, the reactor was heated by a single zone Lindbergh furnace control led by an Omega temperature profile controller. The temperature profile used is depicted in FIG. 4. The ramp rate used was 7° C./min and the final temperature reached was 500° C. At 500° C. the material was soaked for 2 hours. The material was then allowed to cool under helium to room temperature (about 25° C.). After reaching room temperature, the material was washed with acetone and dried overnight in an air oven at 100° C. About 17.6 grams of material was obtained after the drying step.

A visual inspection of the material indicated that the original silica/alumina catalyst had been coated with carbon residue from the pyrolysis of the PFA. The carbon residue is known to be CMS material (see Example 1). Burn off studies in air indicated that the silica/alumina catalyst accounted for about 36% by weight of the CMS/silica/alumina material.

EXAMPLE 3

Silica/alumina catalyst pellets AL-1602 (cylindrical shape, 1/8" diameter×1/8" long) obtained from Harshaw Chemical Company or Engelhard Corp. were calcined in air for eight hours in a muffle furnace. 30.5 grams of the calcined pellets were then placed in a quartz boat and 42.7 grams of PFA resin obtained from Occidental Chemicals (Durez resin #16470) was added to the boat so that the pellets were covered by the PFA. The mixture of pellets and PFA was then placed in a 2.5 inch diameter by 40 inch long quartz reactor. FIG. 3 shows the schematic of the reactor. Helium was flowed through the reactor at 0.25 liters/rain during the heating cycle and the reactor was purged with helium for 5 minutes prior to the start of the heating cycle. After the helium purge, the reactor was heated by a single zone Lindbergh furnace controlled by an Omega temperature profile controller. The temperature profile used is depicted in FIG. 4. The ramp rate used was 7° C./min and the final temperature reached was 500° C. At 500° C. the material was soaked for 2 hours. The material was then allowed to cool under helium to room temperature (about 20° C.). After reaching room temperature, the material was washed with acetone and dried overnight in an air oven at 100° C. The dried pellets were then vigorously shaken in an eight (8) mesh sieve to remove residual carbon. About 48.1 grams of material were obtained after the drying and shaking steps.

A visual inspection of the material indicated that the silica/alumina catalyst pellets had been coated with CMS material. Burn off studies in air in a muffle furnace indicated that the silica/alumina catalyst accounted for about 74% by weight of the CMS/silica/alumina pellets.

41.3 grams of the CMS/silica/alumina pellets obtained from the first PFA pyrolysis step (described immediately above) were mixed with 29.4 grams of PFA and the mixture was placed in a quartz boat. The quartz boat was then placed in the quartz reactor (described above) and subjected to the same helium purge and heating cycle described earlier in this example. After cooling to room temperature (about 18° C.), the material was washed with acetone and dried overnight in an air oven at 100° C. About 49.0 grams of material was obtained after the drying step.

A visual inspection of the material indicated that the CMS/silica/alumina pellets had been coated with additional CMS material. Burn off studies in air indicated that the silica/alumina catalyst accounted for about 71.5% by weight of the final CMS/silica/alumina pellets (i.e., the CMS/silica/alumina pellets obtained after the second PFA pyrolysis step).

Several of the final CMS/silica/alumina pellets were split open using a knife. A visual inspection of the cross section of the pellets revealed that the carbon on the outer surface of the pellet was shiny whereas the carbon that was present in some of the interior porosity was dull in appearance (i.e., not shiny).

EXAMPLE 4

Silica/alumina catalyst AL-1602 obtained from Harshaw Chemical Company or Engelhard Corp. was calcined in air for 24 hours at 600° C. and then crushed in a ball mill overnight to obtain −400 mesh powder. 12 grams of the −400 mesh silica/alumina powder was mixed with 38 grams of polyfurfuryl alcohol (PFA) resin obtained from Occidental Chemicals (Durez resin #16470). The PFA resin had a viscosity of 200 cp and a specific gravity of 1.21 at room temperature. The mixture was then placed in a quartz boat, about 7 inches long and 0.75 inches deep. The quartz boat was placed in a 2.5 inch diameter by 40 inch long quartz reactor. FIG. 3 shows the schematic of the reactor. Helium was flowed through the reactor at 0.25 liters/min during the heating cycle and the reactor was purged with helium for 5 minutes prior to the start of the heating cycle. After the helium purge, the reactor was heated by a single zone Lindbergh furnace controlled by an Omega temperature profile controller. The temperature profile used is depicted in FIG. 4. The ramp rate used was 7° C./min and the final temperature reached was 500° C. At 500° C. the material was soaked for 2 hours. The material was then allowed to cool under helium to room temperature (about 18° C.). After reaching room temperature, the material was washed with acetone and dried overnight in an air oven at 100° C. About 23.3 grams of material was obtained after the drying step.

A visual inspection of the material indicated that the original silica/alumina catalyst had been coated with carbon residue (CMS material) from the pyrolysis of the PFA.

The CMS/silica/alumina material was then crushed to a very fine powder (about −200 mesh) using a Waring commercial blender. About 22.8 grams of the crushed CMS/silica/alumina powder was then mixed with about 15.8 grams of PFA and this mixture was placed in a quartz boat. The quartz boat was then placed in a quartz reactor and subjected to the same helium purge and heating cycle described earlier in this example. After the resulting material had cooled to room temperature (about 21° C.), the material was washed with acetone and dried overnight in an air oven at 100° C. About 26.9 grams of material was obtained after the drying step.

A visual examination of the material indicated that the CMS/silica/alumina material from the first PFA pyrolysis step had been coated with additional CMS material. Burn off studies in air indicated that the silica/alumina catalyst accounted for about 40.7% by weight of the final CMS/silica/alumina material (i.e., the CMS/silica/alumina material obtained after the second PFA pyrolysis step).

EXAMPLE 5

Silica/alumina catalyst AL-1602 obtained from Hershaw Chemical Company or Engelhard Corp. was calcined in air for 24 hours at 600° C. and then crushed in a ball mill overnight to obtain −400 mesh powder. 34 grams of the −400 mesh silica/alumina powder was mixed with 33.8 grams of polyfurfuryl alcohol (PFA) resin obtained from Occidental Chemicals (Durez resin #16470). The PFA resin had a viscosity of 200 cp and a specific gravity of 1.21 at room temperature. The mixture was then placed in a quartz boat, about 7 inches long and 0.75 inches deep. The quartz boat was placed in a 2.5 inch diameter by 40 inch long quartz reactor. FIG. 3 shows the schematic of the reactor. Helium was flowed through the reactor at 0.25 liters/min during the heating cycle and the reactor was purged with helium for 5 minutes prior to the start of the heating cycle. After the helium purge, the reactor was heated by a single zone Lindbergh furnace controlled by an Omega temperature profile controller. The temperature profile used is depicted in FIG. 4. The ramp rate used was 7° C./min and the final temperature reached was 500° C. At 500° C. the material was soaked for 2 hours. The material was then allowed to cool under helium to room temperature (about 19° C.). After reaching room temperature, the material was washed with acetone and dried overnight in an air oven at 100° C. About 47.9 grams of material was obtained after the drying step.

A visual inspection of the material indicated that the original silica/alumina catalyst had been coated with carbon residue from the pyrolysis of the PFA. This carbon residue is known to be CMS material.

The CMS/silica/alumina material was then ground in a Waring commercial blender to a mesh size of <200 mesh. 42.9 grams of the thus ground CMS/silica/alumina material was then mixed with 16.4 grams of PFA resin and this mixture was then placed in a quartz boat and subjected to the same helium purge and heating cycle described earlier in this example. After the resulting material had cooled to room temperature (about 22° C.) it was washed with acetone and dried overnight in an air oven at 100° C. About 46.2 grams of material were obtained after the drying step.

A visual inspection of the material indicated that the original CMS/silica/alumina material had been further coated with additional CMS material. Burn off studies in air indicated that the silica/alumina catalyst material accounted for about 60% by weight of the final CMS/silica/alumina material (i.e., the CMS/silica/alumina material obtained after the second PFA pyrolysis step).

EXAMPLE 6

Silica/alumina catalyst AL-1602 obtained from Harshaw Chemical Company or Engelhard Corp. was calcined in air for 24 hours at 600° C. and then crushed in a ball mill overnight to obtain −400 mesh powder. 12 grams of the −400 mesh silica/alumina powder was mixed with 37.7 grams of polyfurfuryl alcohol (PFA) resin obtained from Occidental Chemicals (Durez resin #16470). The PFA resin had a viscosity of 200 cp and a specific gravity of 1.21 at room temperature. The mixture was then placed in a quartz boat, about 7 inches long and 0.75 inches deep. The quartz boat was placed in a 2.5 inch diameter by 40 inch long quartz reactor. FIG. 3 shows the schematic of the reactor. Helium was flowed through the reactor at 0.25 liters/min during the heating cycle and the reactor was purged with helium for 5 minutes prior to the start of the heating cycle. After the helium purge, the reactor was heated by a single zone Lindbergh furnace controlled by an Omega temperature profile controller. The temperature profile used is depicted in FIG. 4. The ramp rate used was 7° C./min and the final temperature reached was 500° C. At 500° C. the material was soaked for 2 hours. The material was then allowed to cool under helium to room temperature (about 22° C.). After reaching room temperature, the material was washed with acetone and dried overnight in an air oven at 100° C. About 24.1 grams of material was obtained after the drying step.

A visual inspection of the material indicated that the original silica/alumina catalyst had been coated with carbon residue from the pyrolysis of the PFA. This carbon residue is known to be CMS material.

The CMS/silica/alumina material was then ground in a Waring commercial blender to a mesh size of about −200 mesh. 24.1 grams of the thus ground CMS/silica/alumina material was then mixed with 15.5 grams of PFA resin and this mixture was then placed in a quartz boat and subjected to the same helium purge and heating cycle described earlier in this example. After the resulting material had cooled to room temperature (about 22° C.) it was washed with acetone and dried overnight in an air oven at 100° C. About 27.6 grams of material were obtained after the drying step.

A visual inspection of the material indicated that the original CMS/silica/alumina material had been further coated with additional CMS material. Burn off studies in air indicated that the silica/alumina catalyst material accounted for about 45% by weight of the final CMS/silica/alumina material (i.e., the CMS/silica/alumina material obtained after the second PFA pyrolysis step).

EXAMPLE 7

The following Table (i.e., Table 2) compares the conversion of equal molar ammonia/methanol feed over 24.8 grams of less than 30 and greater than 50 (<30, >50) mesh catalyst of this invention (i.e., 18.9 grams of the material formed in Example 6 and 5.9 grams of the material formed in Example 4) with 4.83 grams of <30, >50 mesh uncoated silica/alumina catalyst (i.e., AL-1602 obtained from Harshaw Chemical Company and now available from Engelhard Corp.; 94% by weight alumina and 6% by weight silica) in a 0.250 inch outer diameter and 0.180 inch inner diameter tubular reactor heated in a fluidized sand bath at 400° C. and maintained at 350 psig to give 94.7% and 95.8% methanol conversion respectively. The selectivity improvement is summarized in Table 2 and is measured as a molar ratio of the desired mono- and dimethylamines to trimethylamine.

TABLE 2

| Catalyst | Methanol Conversion | Molar Ratio of Mono + Dimethylamine Trimethylamine |
|---|---|---|
| CMS Coated | 94.7% | 3.30 |
| Uncoated | 95.8% | 1.05 |

EXAMPLE 8

The following Table (i.e., Table 3) compares the conversion of equal molar ammonia/methanol feed over 17.97 grams of <30>50 mesh catalyst of this invention (i.e., the material formed in Example 4) with 4.53 grams of <30, >50 mesh uncoated silica/alumina catalyst (i.e., AL-1602 obtained from Harshaw Chemical Company and now available from Engelhard Corp.; 94% by weight alumina and 6% by weight silica) in a 0.250 inch outer diameter and 0.180 inch inner diameter tubular reactor heated in a fluidized sand bath at 400° C. and maintained at 350 psig to give 64.2% and 64.5% methanol conversion respectively. The selectivity improvement is summarized in Table 3 and is measured as a molar ratio of the desired mono- and dimethylamines to trimethylamine.

TABLE 3

| Catalyst | Methanol Conversion | Molar Ratio of Mono + Dimethylamine Trimethylamine |
|---|---|---|
| CMS Coated | 64.2% | 5.07 |
| Uncoated | 64.5% | 1.95 |

What is claimed is:

1. A method of making a carbon molecular sieve/$SiO_2$/$Al_2O_3$ catalyst material comprising
   a) mixing $SiO_2$/$Al_2O_3$ catalyst material with a precursor material to form a mixture;
   b) heating said mixture to pyrolyze the precursor material and form a carbon molecular sieve/$SiO_2$/$Al_2O_3$ material;
   c) comminuting the carbon molecular sieve/$SiO_2$/$Al_2O_3$ material formed in step b);
   d) mixing the comminuted carbon molecular sieve/$SiO_2$/$Al_2O_3$ material from step c) with additional precursor material to form a second mixture; and
   e) heating said second mixture to pyrolyze the additional precursor material and form additional carbon molecular sieve material on said comminuted carbon molecular sieve/$SiO_2$/$Al_2O_3$ material.

2. The method of claim 1, wherein said precursor material is at least one material selected from the group consisting of polyacrylonitrile, phenol formaldehyde resin, polyvinylidene chloride and polyfurfuryl alcohol.

3. The method of claim 1, wherein said method further comprises the following additional steps:
   comminuting the carbon molecular sieve/$SiO_2$/$Al_2O_3$ catalyst material obtained in step e) in a second comminuting step;
   mixing the comminuted carbon molecular sieve/$SiO_2$/$Al_2O_3$ material obtained in the second comminuting step with additional precursor material to form a third mixture; and
   heating said third mixture to pyrolyze the precursor material to form additional carbon molecular sieve material on said comminuted carbon molecular sieve/$SiO_2$/$Al_2O_3$ material that was obtained in the second comminuting step.

4. The method of claim 3, wherein said comminuting, mixing and heating steps are performed more than two times to form additional carbon molecular sieve material.

5. The method of claim 1, further comprising mixing the carbon molecular sieve/$SiO_2$/$Al_2O_3$ material formed in step e) with additional precursor material, without comminuting the carbon molecular sieve/$SiO_2$/$Al_2O_3$ material formed in step e), to form a third mixture and heating said third mixture to pyrolyze the additional precursor material to form additional carbon molecular sieve material on the carbon molecular sieve/$SiO_2$/$Al_2O_3$ material formed in step e).

6. The method of claim 5, wherein said mixing and heating steps are performed more than two times to form additional carbon molecular sieve material on said carbon molecular sieve/$SiO_2$/$Al_2O_3$ material.

7. A method of making a carbon molecular sieve/$SiO_2$/$Al_2O_3$ catalyst material comprising dropping hot pellets of a $SiO_2$/$Al_2O_3$ catalyst material into a body of precursor material, wherein said precursor material is a material that will form carbon molecular sieve material when subjected to pyrolysis.

8. The method of claim 7, wherein said hot pellets are at a temperature of from about 400° to 800° C.

9. The method of claim 7, wherein said hot pellets are at a temperature of from about 500° to 800° C.

10. The method of claim 7, wherein said hot pellets are at a temperature of from about 600° to 800° C.

11. The method of claim 7, wherein the carbon molecular sieve/$SiO_2$/$Al_2O_3$ catalyst material formed after the hot pellets are dropped into the precursor material is in the form of coated pellets.

12. The method of claim 11, wherein the coated pellets are heated to an elevated temperature and dropped into a body of precursor material that will form carbon molecular sieve material when subjected to pyrolysis.

13. The method of claim 12, wherein said heating and dropping steps are performed more than two times to form additional carbon molecular sieve material on said coated pellets.

14. The method of claim 7, wherein said precursor material is at least one material selected from the group consisting of polyacrylonitrile, phenol formaldehyde resins polyvinylidene chloride and polyfurfuryl alcohol.

15. The method of claim 12, wherein said precursor material is at least one material selected from the group consisting of polyacrylonitrile, phenol formaldehyde resin, polyvinylidene chloride and polyfurfuryl alcohol.

* * * * *

UNITED STATES PATENT AND TRADEMARK OFFICE
CERTIFICATE OF CORRECTION

PATENT NO. : 5,470,814
DATED : November 28, 1995
INVENTOR(S) : Foley, et al

It is certified that error appears in the above-indentified patent and that said Letters Patent is hereby corrected as shown below:

On the cover page, in section [54] "CMS/SIO$_2$/AL$_2$O$_3$" should be --CMS/SiO$_2$/Al$_2$O$_3$--.

In Column 7, line 1, "embodiment$^{MMA}$" should be --embodiment--.

In Column 16, line 39, "resins" should be --resin,--.

Signed and Sealed this

Fifteenth Day of October, 1996

Attest:

BRUCE LEHMAN

*Attesting Officer*   *Commissioner of Patents and Trademarks*